United States Patent
Renz

(10) Patent No.: US 7,834,626 B2
(45) Date of Patent: Nov. 16, 2010

(54) MAGNETIC RESONANCE SYSTEM WITH AN RF SHIELD HAVING FEEDTHROUGHS FOR ANTENNA FEED LINES AND RF CIRCUITRY COOLED BY THE GRADIENT COIL COOLING SYSTEM

(75) Inventor: Wolfgang Renz, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 201 days.

(21) Appl. No.: 11/950,672

(22) Filed: Dec. 5, 2007

(65) Prior Publication Data

US 2008/0136418 A1 Jun. 12, 2008

(30) Foreign Application Priority Data

Dec. 11, 2006 (DE) .................. 10 2006 058 329

(51) Int. Cl.
*G01V 3/00* (2006.01)
(52) U.S. Cl. ..................................... 324/318; 324/322
(58) Field of Classification Search ......... 324/300–322; 600/407–435; 333/219–235; 439/581
See application file for complete search history.

(56) References Cited

U.S. PATENT DOCUMENTS

| | | | | |
|---|---|---|---|---|
| 3,402,346 | A * | 9/1968 | Baker | 324/322 |
| 5,280,247 | A * | 1/1994 | DeMeester et al. | 324/318 |
| 5,483,163 | A | 1/1996 | Wen et al. | 324/318 |
| 6,496,006 | B1 * | 12/2002 | Vrijheid | 324/318 |
| 6,900,636 | B2 | 5/2005 | Leussler | 324/318 |
| 6,998,842 | B2 * | 2/2006 | Sinnema et al. | 324/318 |
| 7,282,916 | B2 * | 10/2007 | Eberlein et al. | 324/318 |
| 7,301,343 | B1 * | 11/2007 | Sellers | 324/318 |
| 7,367,839 | B2 * | 5/2008 | Greim et al. | 439/581 |
| 7,397,244 | B2 * | 7/2008 | Cirel | 324/318 |
| 2005/0033152 | A1 * | 2/2005 | Sinnema et al. | 600/410 |
| 2005/0104590 | A1 * | 5/2005 | Sinnema et al. | 324/318 |
| 2005/0179512 | A1 * | 8/2005 | Weyers et al. | 335/300 |
| 2005/0258832 | A1 * | 11/2005 | Eberlein et al. | 324/318 |
| 2006/0082370 | A1 * | 4/2006 | Cirel | 324/318 |
| 2006/0238198 | A1 | 10/2006 | Nabetani | 324/318 |
| 2007/0026733 | A1 * | 2/2007 | Greim et al. | 439/581 |
| 2008/0136418 | A1 * | 6/2008 | Renz | 324/322 |
| 2009/0184713 | A1 * | 7/2009 | Tigwell | 324/318 |

FOREIGN PATENT DOCUMENTS

WO WO 2005/012931 2/2005

* cited by examiner

*Primary Examiner*—Brij B. Shrivastav
*Assistant Examiner*—Tiffany A Fetzner
(74) *Attorney, Agent, or Firm*—Schiff Hardin LLP

(57) ABSTRACT

A magnetic resonance system for generation of magnetic resonance exposures of an examination subject in a patient positioning region has an antenna structure with a number of antenna elements arranged in the patient positioning region. Feed lines respectively supply the antenna elements with radio-frequency signals for emission of a radio-frequency field in the patient positioning region and/or to accept radio-frequency signals acquired by the antenna elements. The magnetic resonance system also has a radio-frequency shielding that shields an external region outside of the patient positioning region from radio-frequency signals radiated in the patient positioning region. This radio-frequency shielding has a number of feedthroughs through which the feed lines are respectively directed from the external region over a short distance to the antenna elements.

11 Claims, 3 Drawing Sheets

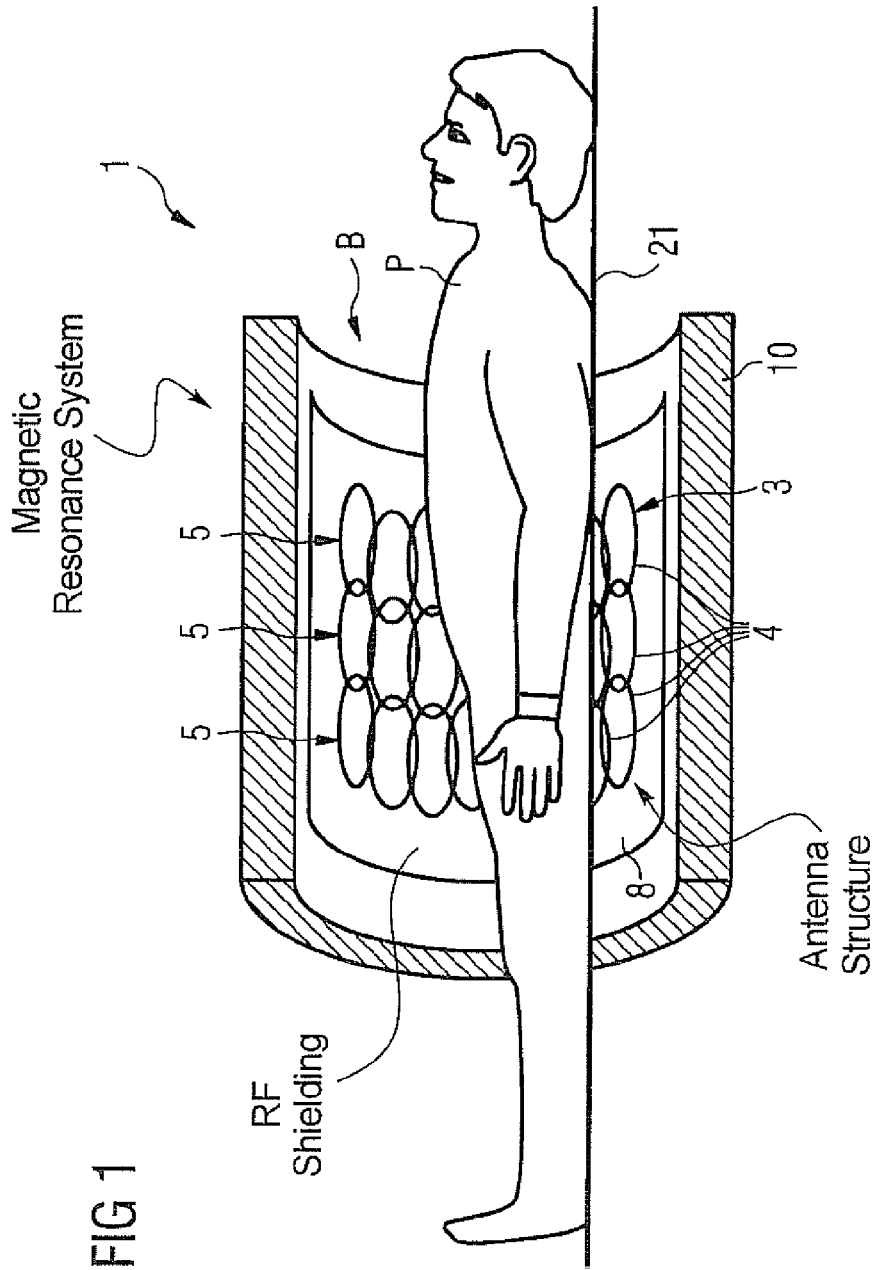

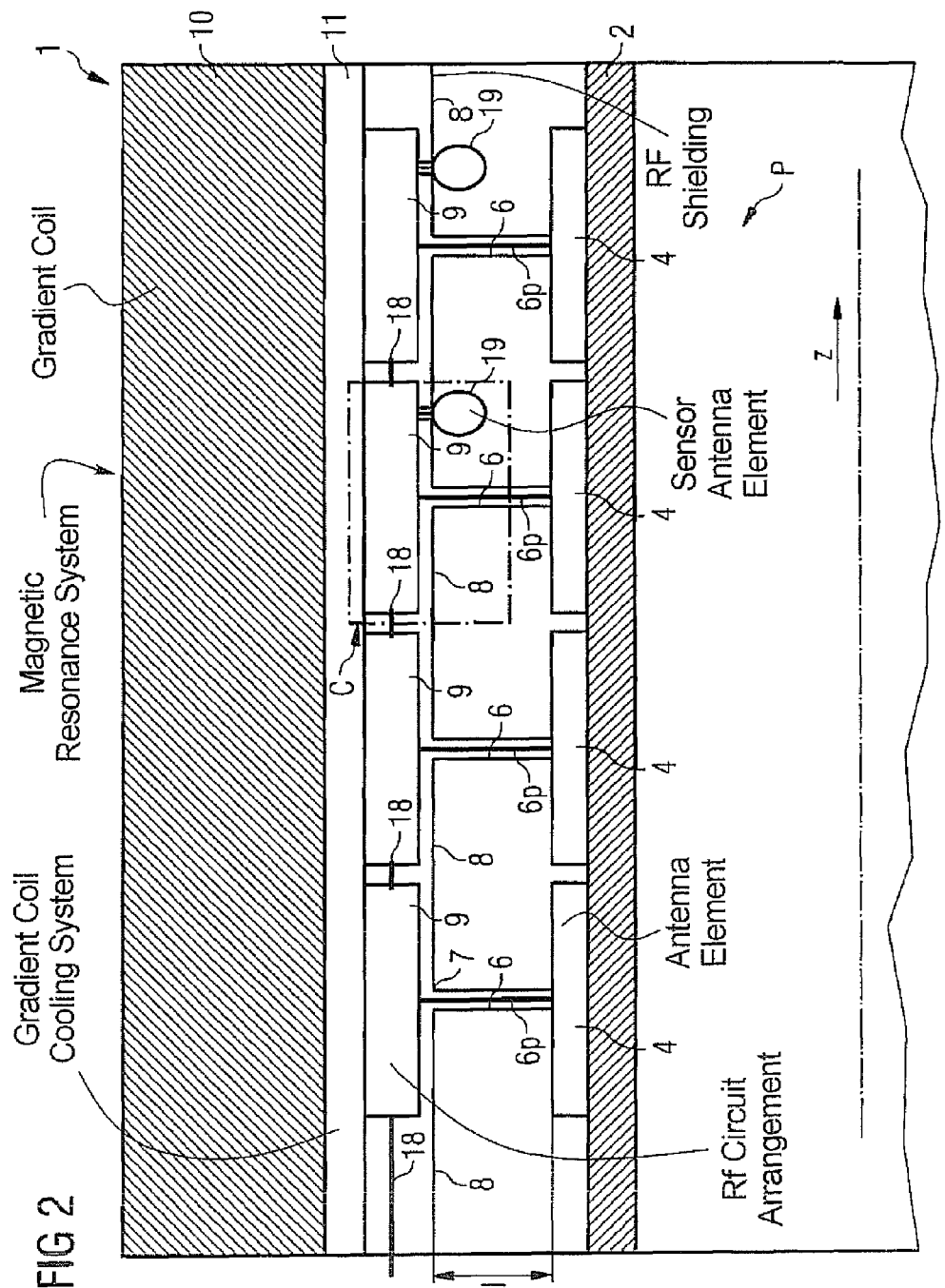

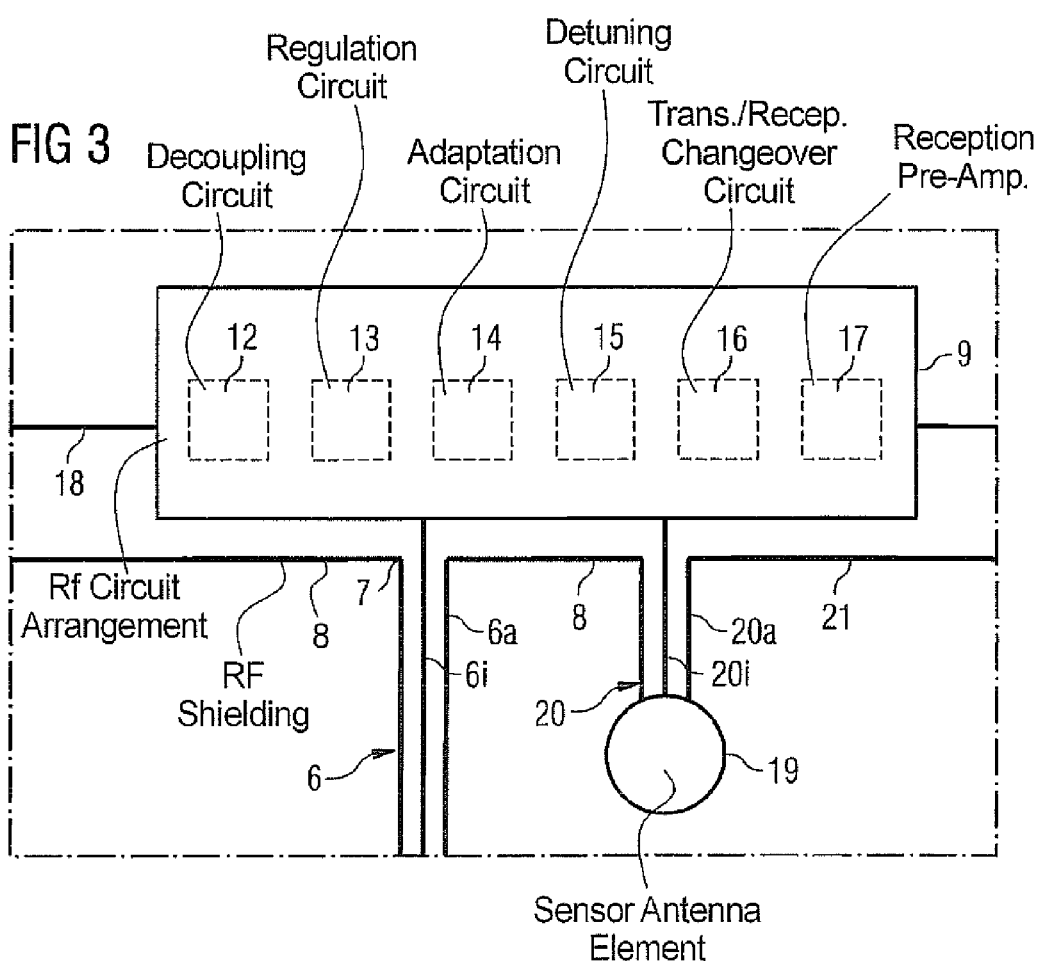

MAGNETIC RESONANCE SYSTEM WITH AN RF SHIELD HAVING FEEDTHROUGHS FOR ANTENNA FEED LINES AND RF CIRCUITRY COOLED BY THE GRADIENT COIL COOLING SYSTEM

BACKGROUND OF THE INVENTION

1. Field of the Invention

The present invention concerns a magnetic resonance (MR) system for generation of magnetic resonance exposures of an examination subject in a patient positioning region. The magnetic resonance system is of the type having an antenna structure with a number of antenna elements arranged in the patient positioning region feed lines that respectively supply the antenna elements with radio-frequency signals for emission of a radio-frequency field in the patient positioning region and/or to accept radio-frequency signals acquired by the antenna elements; and a radio-frequency shielding that shields an external region outside of the patient positioning region from radio-frequency signals radiated in the patient positioning region.

2. Description of the Prior Art

Magnetic resonance tomography is a widely used technique for acquisition of images of the inside of the body of a living examination subject. In order to acquire an image with this method, the body or the body part of the patient or examination subject must initially be exposed to an optimally homogeneous static basic magnetic field which is generated by a basic field magnet of the magnetic resonance system. Rapidly switched gradient fields for spatial coding that are generated by gradient coils are superimposed on this basic magnetic field during the acquisition of the magnetic resonance images. Moreover, radio-frequency pulses of a defined field strength are radiated into the examination subject with radio-frequency antennas. The nuclear spins of the atoms in the examination subject are excited by means of these radio-frequency pulses such that they are deflected from their equilibrium state parallel to the basic magnetic field by "excitation flip angle". The nuclear spins then precess around the direction of the basic magnetic field. The magnetic resonance signals generated upon relaxation in the initial position are acquired by radio-frequency reception antennas. The magnetic resonance images of the examination subject are generated on the basis of the acquired magnetic resonance signals.

A typical magnetic resonance tomography apparatus has a patient positioning region (also called a patient space in the following) in which is located a patient bed on which the patient is positioned during the examination. For example, this can be a "patient tunnel" in a tube running through the housing of the tomography apparatus. Moreover, hoe are also MR tomograph apparatuses with a laterally open patient positioning region that is enclosed in a U-shape structure formed by the housing of the MR tomography. A number of coils and possibly also permanent magnets for generation of the necessary basic magnetic field and the gradient fields are typically located within the housing of the tomography apparatus.

Furthermore, the tomography apparatus typically has an antenna structure permanently installed in the housing, with which antenna structure the necessary radio-frequency pulses are emitted into the patient positioning region and the induced magnetic resonance signals can be acquired. This radio-frequency antenna is also known as a "body coil". Such a body coil, for example, frequently has a used birdcage structure composed of a number of conductor rods arranged around the patient space and running parallel to the primary field direction. The conductor rods are connected with one another by annular conductors at the front sides of the coils. Other structures such as, for example, saddle coils are known. In order to shield the external region outside of the patient positioning region from the $B_1$ field (i.e. the radio-frequency field) that is generated by the antenna structure and in order to minimize interference from the external region during MR signal acquisition, the patient positioning region is typically surrounded by a radio-frequency shielding normally at ground potential. For example, the shielding can be thin copper layers or the like. Since, as already described in the preceding, the tomography apparatus housing normally extends annularly or in some embodiments in a U-shape around the patient positioning region, this radio-frequency shielding either annularly or partially encloses the patient space.

In conventional MR systems the feed of the radio-frequency antenna with radio-frequency signals has previously normally ensued via two feed lines that are directed in the longitudinal direction of the patient positioning region within the shielded patient positioning region and, for example, outward to radio-frequency circuit arrangements at the front side of the apparatus. The radio-frequency circuit arrangements typically have radio-frequency power amplifiers and possibly further circuit components in order to control the antenna structure and to monitor and/or pre-process signals acquired by the antenna structure.

Moreover, in addition to these permanently installed antenna structures there are also local coils that are arranged optimally close to the patient or subject, i.e. are moved with the patient into the patient positioning region.

An example of such a local coil is a head coil as disclosed in U.S. Pat. No. 5,483,163. The coil described there is specifically designed as a small birdcage structure, and the antenna elements running in the longitudinal direction are fashioned not as rods but rather as individually pivotable conductor loops in order to be able to detune the head coil.

Further examples for local coils are provided in WO 2005/012931 A1. Among other things, a surface coil is described therein for placement on or to be placed under a patient, this surface coil having an array of individual conductor loops. For inductive decoupling the conductor loops are shaped in specific geometries and arranged in a specific manner relative to one another, so as to overlap.

In principle local coils, can be used both for transmission of the excitation pulse sequences and for acquisition of the magnetic resonance signals. Due to the smaller distance from the examination subject, they normally have a better reception quality than the permanently installed body coil. In most cases the body coil is therefore used to emit the excitation pulse sequences and the local coils serve to acquire the magnetic resonance signals. In such a method the local coils must be deactivated during the transmission procedure and the body coil must be activated. In reverse, upon acquisition the local coils must be activated and the body coil must be deactivated. The deactivation of a coil can ensue by sufficiently detuning it relative to the magnetic resonance frequency. For this purpose, the coils are equipped with switching devices. Such a switching device is described in DE 10 2006 019 173.

In order to be able to influence the structure of the radiated magnetic field with optimal detail in a suitable manner in all regions of the examination volume, in order to achieve an optimally good homogeneity of the $B_1$ field in the examination volume, the trend of future developments in the field of magnetic resonance systems is moving toward using a number of separately-controllable antenna elements for emission of the radio-frequency signals instead of a simple antenna structure that can be controlled via only two feed lines. An example of this is described in DE 101 24 465 A 1, which discloses an arrangement for generation of radio-frequency fields in the examination volume of an MR apparatus that has a number of separately-controllable resonator segments (i.e. antenna elements). The resonator segments are arranged in a birdcage antenna around the patient space and are respectively formed by at least one conductor element running in parallel.

The use of a number of separately controllable antenna elements simultaneously entails an increase of the number of feed lines to the antenna elements. The previously typical direction of the feed lines (usually executed in the form of coaxial lines) to the antenna elements in the longitudinal direction in the patient space is therefore disadvantageous for multiple reasons. Space problems arise due to the increase of the feed lines to the antenna elements within the patient space. In part it is necessary that the feed lines intersect, and this can lead to interference due to crosstalk. Moreover, asymmetrical currents that can influence the magnetic resonance acquisitions in an unwanted manner can typically occur on the outer conductors of the feed lines due to this manner of the direction and the length of the feed lines. At least the latter cited problem was previously solved by the use of sheath wave barriers (known as baluns) with high impedances that prevent the propagation of unwanted waves on the external conductors. However, this incurs additional costs for the installation of the sheath wave barriers and requires additional space.

SUMMARY OF THE INVENTION

An object of the present invention is to improve an MR tomography apparatus of the aforementioned type so that the aforementioned problems are avoided or at least significantly reduced in a simple, safe, cost-effective and space-saving manner.

As already described, for generation of magnetic resonance exposures of an examination subject in the patient positioning region, the inventive magnetic resonance system has an antenna structure (i.e. a body coil) permanently installed in the tomography apparatus housing, with a number of antenna elements arranged in the patient positioning region, and has feed lines to respectively supply the antenna elements with radio-frequency signals for emission of a radio-frequency field in the patient positioning region and/or to accept radio-frequency signals acquired by the antenna elements. The magnetic resonance system also has a radio-frequency shielding that shields an external region outside of the patient positioning region in which the patient bed is located from radio-frequency signals radiated in the patient positioning region. According to the invention, this radio-frequency shielding has a number of feedthroughs through which the feed lines are respectively directed from the external region over a short distance to the antenna elements.

Due to the short length of the segments of the feed lines within the patient positioning region, i.e. within the region surrounded by the radio-frequency shielding, crosstalk and coupling of unwanted electromagnetic disturbance variables can be precluded to a large extent in a simple and safe manner. Additionally, significantly less space is required than for the typical direction of the feed lines in the longitudinal direction of the patient positioning region and leading them through at the front sides.

In a preferred exemplary embodiment, at least some feed lines (advantageously all feed lines) are executed as coaxial lines. For this purpose, the outer conductors of the coaxial line and the radio-frequency shielding in the region of the feedthroughs preferably has cooperating elements in order to electrically connect the outer conductors of the coaxial line and the radio-frequency shielding. The connections are advantageously executed such that they can be detached. For this purpose the connection can be, for example, a screw connection or a bayonet connection or the like. Connections also can be produced via soldering, welding, conductive adhesive or other methods.

The segments of the feed lines in the patient space, i.e. from the feedthrough through the radio-frequency shielding up to the respective antenna element, are advantageously dimensioned such that a maximum length results that is $1/10$ (preferably a maximum length of $1/20$) of the wavelength $\lambda$ of the emitted radio-frequency signals or of the acquired MR signals results. This corresponds to a length of at maximum $1/5$ (particularly preferably at maximum $2/5$) of the critical length of $\lambda/4$. A sufficiently safe length is thus still maintained to prevent amplified interferences on the feed lines from occurring. For the radio-frequency signals at 123 MHz (given a basic magnetic field of 3T) used in typical $H_1$ imaging given a propagation speed of approximately $2.8 \times 10^8$ m/s in the radio-frequency lines, a wavelength $\lambda$ of approximately 230 cm results and therewith a preferred maximum length of the segment of the feed line in the patient space of at maximum approximately 23 cm, particularly preferably a maximum approximately 12 cm.

In a preferred exemplary embodiment at least one part of the antenna elements is arranged annularly around the patient space. Other embodiments can be an arrangement in which the antenna elements are, for example, arranged in a partial circle around the patient space.

Also preferred is an arrangement in which at least some of the antenna elements are arranged next to one another along the examination subject in the longitudinal direction of the tomography apparatus in order to also be able to adjust the desired homogeneity of the $B_1$ radio-frequency field in detail in the longitudinal direction of the tomograph.

Also advantageous is an antenna structure in which a group of antenna elements is respectively annularly arranged around the patient space and a number of such groups of antenna elements are arranged one after another in the longitudinal direction of the patient space. More precise adjustments of the B1 field in all three spatial directions can be made therewith. The groups of antenna elements can couple as modules in the longitudinal direction. Due to the modular design of the antenna elements, these can be produced and installed particularly efficiently.

A radio-frequency circuit arrangement for the antenna structure is preferably arranged outside of the radio-frequency shielding, adjacent to a portion of the antenna structure that is associated with the appertaining radio-frequency circuit arrangement. This radio-frequency circuit arrangement has a radio-frequency power amplifier in order to deliver the necessary transmission power. For example, respectively separate radio-frequency circuit arrangements can be associated with the individual antenna elements, or possibly the group of antenna elements, which are, for example, annularly arranged around the patient space. The respective separate radio-frequency circuit arrangements are positioned adjacent to the appertaining antenna elements or antenna element groups outside of the radio-frequency shielding.

The arrangement of radio-frequency circuit arrangements for the various antenna elements or groups of antenna elements in proximity to the antenna elements or groups of antenna elements, allows not only the cable length of the feed lines within the patient space, but also the total length of the feed lines, to be kept short. The losses in the feed lines are then minimal and can nearly be disregarded.

In a preferred exemplary embodiment, the radio-frequency circuit arrangement (advantageously all radio-frequency circuit arrangements) is/are arranged for the antenna structure such that the cooling of the appertaining radio-frequency circuit arrangement can ensue with a gradient coil cooling system that is normally present anyway. A separate cooling device for the radio-frequency circuit arrangements is then not required.

Each radio-frequency circuit arrangements can have a regulation circuit that regulates the radio-frequency field emitted by the associated antenna elements or the associated group of antenna elements. The regulation circuit can advantageously be integrated into the housing of the appertaining radio-frequency circuit arrangement. Alternatively it can be executed as a separate circuit unit.

Real values of the radio-frequency field that represent the radio-frequency field emitted by the antenna structure are required for such a regulation. These measurement values can be the phase and the amplitude of the radio-frequency field. One or more sensor antenna elements (also called pick-up coils) are used for the acquisition of the real values. The pick-up coils are connected with the radio-frequency circuit arrangements via feed lines executed as coaxial lines. Further feedthroughs through which the feed lines are directed from the pick-up coils to the radio-frequency circuit arrangements in very short paths are advantageously located in the radio-frequency shielding adjacent to the pick-up coils. In the region of the feedthroughs the outer conductors of the coaxial line and the radio-frequency shielding can have cooperating elements in order to electrically connect the outer conductors of the coaxial line and the radio-frequency shielding, advantageously via detachable connections.

A separate decoupling circuit and/or a separate adaptation circuit and/or a separate detuning circuit and/or a separate transmission-reception change-over and/or a separate reception pre-amplifier is respectively, advantageously associated with the respective groups of antenna elements (particularly preferably with each antenna element). These are preferably integrated into the respective radio-frequency circuit arrangements, but can also be externally arranged upstream.

The decoupling circuit is required in order to adjust the individual antenna elements such that electromagnetic coupling is prevented between the antenna elements and additional reception coils in the patient region during the acquisition phase. The regulation circuit controls the emission of the radio-frequency field. The adaptation circuit corrects the impedance of the antenna to the impedance of the feed line (which is typically 50 Ohm). The detuning circuit is an active/passive circuit in order to tune the resonance frequency of the appertaining antenna element to the magnetic resonance frequency (for example to 123 MHz) for activation or to detune it for deactivation. The transmission-reception change-over serves for switching the radio-frequency circuit arrangements between trans-mission operation and reception operation. The reception pre-amplifier amplifies the signals acquired by the appertaining antenna elements for later further processing.

BRIEF DESCRIPTION OF THE DRAWINGS

FIG. 1 is a schematic representation of a longitudinal section through a patient tunnel with an antenna structure 3.

FIG. 2 is a schematic, detailed longitudinal section through one half of the patient tunnel according to FIG. 1.

FIG. 3 is an enlarged representation of the section C in FIG. 2.

DESCRIPTION OF THE PREFERRED EMBODIMENTS

FIG. 1 shows a typical patient positioning region B fashioned as a tube-shaped patient tunnel in a magnetic resonance system 1. A patient bed 22 is arranged within this patient tunnel such that it can be displaced along the longitudinal axis of the patient tunnel, on which patient bed 22 a patient or subject P is positioned for examination. For this purpose, the patient bed 22 can be moved out of the patient tunnel at the foot-end and/or head-end front of the patient tunnel. The patient/test subject P is then positioned on the patient bed 22 outside of the patient tunnel and the patient bed 22 with the patient/test subject P is subsequently moved into the patient tunnel. The patient tunnel is bordered by a tube-shaped dividing wall 2 (not shown in FIG. 1) that is composed of, for example, GRP (glass fiber-reinforced plastic).

An antenna structure (for example in the form of conductor foils, plates or the like) is mounted on the outside of the GRP tube facing away from the patient positioning region B. For the most part copper or another metal is used as a conductive material. The shown exemplary embodiment is an antenna structure 3 that has a number of groups 5 of antenna elements 4 in the form of circular coils that are annularly arranged around the patient positioning region B. A number of groups 5 of antenna elements 4 are arranged one after another in the longitudinal direction Z. The individual antenna elements 4 overlap in a suitable manner for electromagnetic decoupling. Other structures are also possible.

The patient positioning region B encloses a gradient coil 10 for generation of a gradient magnetic field. Coils for the primary magnetic field are typically likewise present, however are not shown for better clarity.

Suitable radio-frequency pulses are fed into the antenna structure 3 via feed lines 6 so that the desired radio-frequency field forms within the patient positioning region B. These feed lines 6 are likewise not shown in FIG. 1 for better clarity. The design and the arrangements of the feed lines 6 at the antenna elements 4, however, are shown in FIG. 2.

FIG. 2 shows a schematic longitudinal section through one half of the patient tunnel for clarification of the antenna elements 4 arranged one after another in the longitudinal direction Z. Here the antenna elements 4 are not shown overlapping for better clarity.

The individual antenna elements 4 are electrically connected with radio-frequency circuit arrangements 9 via feed lines 6 that are executed as a coaxial line with an outer conductor 6a and an inner conductor 6i.

These radio-frequency circuit arrangements 9 are arranged outside of the radio-frequency shielding 8 that shields an external region A outside of the patient positioning region B from the radio-frequency signals radiated in the patient positioning region B. The radio-frequency shielding 8 has feedthroughs 7 that are arranged adjacent to the antenna elements 4, through which feedthroughs 7 the feed lines are led in optimally direct (i.e. shortest) paths from the antenna elements 4 out from the patient positioning region 8 and there are connected with the radio-frequency circuit arrangements 9. The feed lines 6 are thereby led through the feedthroughs 7 of the radio-frequency shielding 8 such that the outer conductors 6a of the feed lines 6 are electrically connected in a detachable manner (for example via a screw connection) with the radio-frequency shielding 8 lying at ground potential.

The length l of the segment 5 of the feed lines 6 within the region enclosed by the radio-frequency shielding thereby is less than 13 cm in order to prevent as far as possible a crosstalk on the feed lines 6 as well as a coupling (injection) of other electromagnetic disturbance variables.

The radio-frequency circuit arrangements 9 arranged outside of the radio-frequency shielding 8 are fed via control lines 18 with the information required for generation of the radio-frequency signals as well as with the required voltage. The acquired radio-frequency signals are likewise relayed via suitable RF lines to an evaluation device. Only one line 18 that represents the aforementioned lines or, respectively, RF lines is schematically presented in FIG. 2.

The radio-frequency circuit arrangements 9 comprise typical amplifiers, decoupling circuits 12, regulation circuits 13, adaptation circuits 14, detuning circuits 15 as well as possible further circuits. These are not shown here in FIG. 2 for clarity and are described in detail in connection with FIG. 3.

By the arrangement of the radio-frequency circuit arrangements 9 in the immediate proximity of the gradient coil 10, they can be directly cooled as well by the existing gradient coil cooling system 11. A separate cooling system for the radio-frequency circuit arrangements 9 is thus conserved.

The magnetic resonance system 1 has sensor antenna elements 19 (also called pick-up coils) for acquisition of real values for the control of the antenna elements 4 within the region surrounded by the radio-frequency shielding. Measurement values are therewith acquired that characterize the emitted radio-frequency field. These are typically the amplitude and the phase of the radio-frequency signals. Further feedthroughs 21 into the radio-frequency shielding 8 are located in immediate proximity to the pick-up coils 19. The pick-up coils 19 are connected with the radio-frequency circuit arrangements 9 via coaxial lines 20 with an outer conductor 20*a* and an inner conductor 20*i*. These coaxial lines 20 are directed on the shortest path out through the feedthroughs 21 of the radio-frequency shielding 8. In the region of the feedthroughs 21 the outer conductors 20*a* of the feed lines 20 are electrically connected with the radio-frequency shielding 8 lying at ground potential by means of a preferably detachable connection.

FIG. 3 shows an enlarged representation of the part C (marked in FIG. 2) of the patient tunnel with a radio-frequency circuit arrangement 9. This is fashioned as a radio-frequency power amplifier in order to deliver the required transmission power and, as mentioned above, includes various modules 12, 13, 14, 15, 16, 17.

Among these are, for example, the regulation circuit 13 that is required in order to control the antenna structure with the radio-frequency signals. Likewise located here is a decoupling circuit 12 that adjusts the individual antenna elements 4 such that an electromagnetic coupling between the antenna elements 5 is prevented to the greatest extent possible. Furthermore, the radio-frequency circuit arrangement 9 normally has an adaptation circuit 14 that corrects the impedance of the antenna elements 4 to the impedance of the feed line 6. A further component is a detuning circuit 15 that tunes the resonance frequency of the appertaining antenna element 4 to the magnetic resonance frequency for activation. Further modules are the transmission-reception change-over 16 that switches the radio-frequency circuit arrangement 9 between a transmission mode and a reception mode and a reception preamplifier 17 that pre-amplifies the acquired radio-frequency signals and relays them to an image data acquisition unit in a control computer via the control line 18. This control computer is not shown here. It is typically located in a separate room or chamber in proximity to the described tomography room.

The design of a magnetic resonance system described in the preceding is only an exemplary embodiment which can be modified by various manners by those skilled in the art without departing from the scope of the invention. The invention was explained above in the context of a medically-utilized magnetic resonance tomography apparatus, but is not limited to such applications and can also be utilized in scientific applications.

I claim as my invention:

1. A magnetic resonance system configured to generate a magnetic resonance exposure of an examination subject comprising:
    a magnetic resonance data acquisition unit having an opening therein configured to receive an examination subject in an examination region of the data acquisition system;
    said data acquisition unit comprising a gradient coil system and a gradient coil cooling system that cools said gradient coil system;
    a patient bed, configured to receive a subject thereon, that is movable relative to said opening of said data acquisition unit in order to position a portion of the patient in said examination region;
    an antenna structure, comprising a plurality of antenna elements, permanently installed in said data acquisition unit in said examination region, and separate radio-frequency circuits respectively associated with said antenna elements individually or in groups;
    at least one of said radio-frequency circuits being in thermal communication with said gradient coil cooling system and is cooled by said gradient coil cooling system;
    a plurality of feed lines respectively connected to said antenna elements to feed signals into the respective antenna elements in order to cause the antenna elements to radiate a radio-frequency field in the examination region and/or in order to receive radio-frequency signals acquired by the respective antenna elements from the examination region;
    radio-frequency shielding located in spatial relation to said opening of said data acquisition unit in order to shield an external region outside of said opening from the radiated radio-frequency field;
    said radio-frequency shielding comprising a plurality of feedthroughs therein, through which said feed lines respectively proceed along a distance from said external region to the respective antenna elements; and
    each of said feed lines having at least a portion thereof formed as a coaxial cable having an outer conductor, with the respective outer conductors of the feed lines being in electrical connection with the radio-frequency shielding.

2. A magnetic resonance system as claimed in claim 1 wherein a portion of said feed lines in the opening of said data acquisition unit has a maximum length that is one-tenth of a wavelength of said signals conducted by said feed lines.

3. A magnetic resonance system as claimed in claim 1 wherein a portion of said feed lines in the opening of said data acquisition unit has a maximum length that is one-twentieth of a wavelength of said signals conducted by said feed lines.

4. A magnetic resonance system as claimed in claim 1 wherein at least some of said antenna elements are disposed annularly around said opening of said data acquisition unit.

5. A magnetic resonance system as claimed in claim 1 wherein at least some of said antenna elements are disposed along a longitudinal direction of said opening of said data acquisition unit.

6. A magnetic resonance system as claimed in claim 1 wherein each radio-frequency circuit comprises a regulation circuit that regulates the radio-frequency field emitted by the antenna element or group of antenna elements associated therewith.

7. A magnetic resonance system as claimed in claim 1 wherein each radio-frequency circuit is located outside of said radio-frequency shielding at a location adjacent to the antenna element or group of antenna elements associated therewith.

8. A magnetic resonance system as claimed in claim 1 comprising sensor antenna elements in said opening of said data acquisition unit that acquire measurement values representing a characteristic of the radio-frequency fields emitted by the antenna elements of the antenna structure.

9. A magnetic resonance system as claimed in claim 1 comprising a circuit selected from the group consisting of decoupling circuits, adaptation circuits, detuning circuits, and transmission/reception changeover circuits, respectively connected to said antenna elements or groups of said antenna elements.

10. A magnetic resonance system as claimed in claim 1 wherein said antenna elements are divided into groups of antenna elements that are each annularly disposed around the opening of the data acquisition unit, said groups of antenna elements being disposed next to each other in succession along a longitudinal direction of said opening of said data acquisition unit.

11. A magnetic resonance system as claimed in claim 10 wherein each said group of antenna elements is formed as a module, and wherein said modules are coupled with each other in said longitudinal direction.

* * * * *